United States Patent
Eisenberg

(10) Patent No.: US 8,376,140 B2
(45) Date of Patent: Feb. 19, 2013

(54) PORTABLE POWDER DELIVERY SYSTEM AND METHOD

(75) Inventor: Jordan Eisenberg, Denver, CO (US)

(73) Assignee: Breakthrough Products, Inc., Denver, CO (US)

( * ) Notice: Subject to any disclaimer, the term of this patent is extended or adjusted under 35 U.S.C. 154(b) by 484 days.

(21) Appl. No.: 12/426,417

(22) Filed: Apr. 20, 2009

(65) Prior Publication Data

US 2010/0264055 A1 Oct. 21, 2010

(51) Int. Cl.
- *A61J 1/14* (2006.01)
- *A61K 31/60* (2006.01)
- *A61K 31/29* (2006.01)
- *A61K 33/10* (2006.01)
- *A61K 31/451* (2006.01)
- *A61K 31/138* (2006.01)
- *A61K 31/167* (2006.01)
- *A61K 31/7016* (2006.01)

(52) U.S. Cl. ........ 206/532; 514/503; 514/648; 514/629; 514/53; 514/165; 514/327; 424/687; 220/560.01

(58) Field of Classification Search .................. None
See application file for complete search history.

(56) References Cited

U.S. PATENT DOCUMENTS

| | | | |
|---|---|---|---|
| 2003/0098257 A1* | 5/2003 | Robertson | 206/538 |
| 2004/0159575 A1 | 8/2004 | Shudo et al. | |
| 2006/0103130 A1* | 5/2006 | Koivukunnas et al. | 283/81 |
| 2009/0241483 A1* | 10/2009 | Detwiler et al. | 53/492 |
| 2010/0326877 A1* | 12/2010 | Hemmerlin et al. | 206/532 |

FOREIGN PATENT DOCUMENTS

| | | |
|---|---|---|
| JP | 09-299445 | 11/1997 |
| JP | 2002-145762 | 5/2002 |
| JP | 2005-087570 | 4/2005 |

OTHER PUBLICATIONS

International Report on Patentability for PCT Application No. PCT/US2010/031750, Oct. 25, 2011.
Written Opinion for PCT Application No. PCT/US2010/031750, Jan. 24, 2011.
International Search Report for PCT Application No. PCT/US2010/031750, Jan. 24, 2011.

* cited by examiner

*Primary Examiner* — Suzanne Ziska
(74) *Attorney, Agent, or Firm* — Brownstein Hyatt Farber Schreck, LLP

(57) ABSTRACT

A vehicle to carry a powered medication that addresses the limitations of the prior art. It includes a system and method. A powder delivery system includes a first panel and a second panel coupled together around a periphery of the panels to form a sealed void therebetween, each the panel having a width and length about equal to a standard credit card width and length, respectively; and a powder, disposed in the void, having a quantity at least about equal to an active dose of the powder; wherein a thickness of the panels with the powder disposed therebetween is not greater than about 0.1 inches and more preferably not greater than about 0.03 inches.

18 Claims, 1 Drawing Sheet

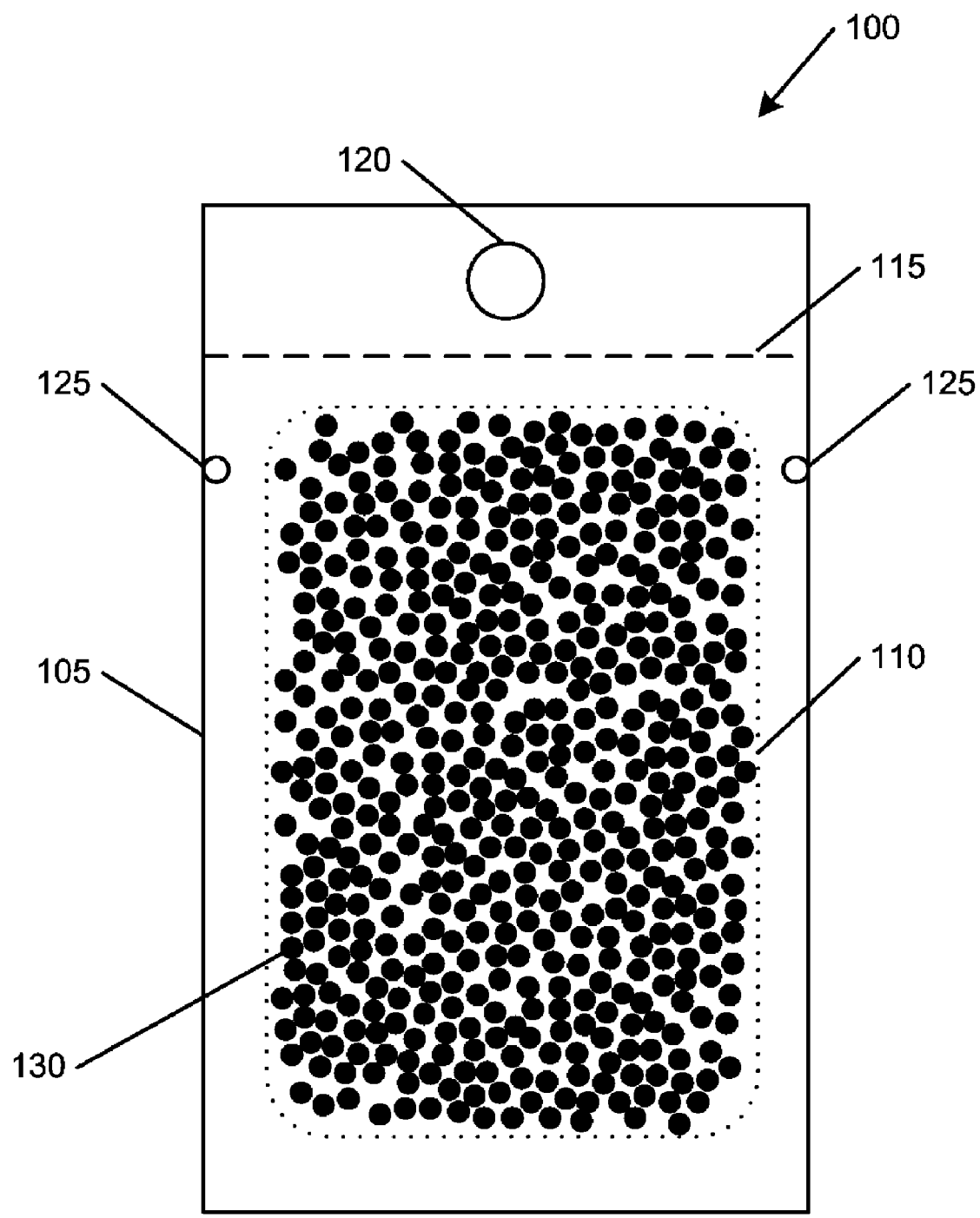

PORTABLE POWDER DELIVERY SYSTEM AND METHOD

BACKGROUND OF THE INVENTION

The present invention relates generally to powder delivery and more specifically to medicament storage in a wallet for emergency access.

It is known to purchase over the counter medications in pill form. Typically these medications are sold in a box or in a single or few use dose package containing a small number (e.g., 1-2) pills or tablets.

Currently there are no medications in pill, tablet, or capsule form that are convenient for a user to take with them whenever leaving the home, office, or drug store where these medicines may be generally available. Moreover, the odds of the user having a serious medical emergency when out of the home or office or drug store where these medicines may be generally available can be significant, and thus there is an important need for a way to conveniently, unobtrusively and easily carry such "emergency medications" on the person, so that they have medication accessible in the case of emergency (specifically (for example), aspirin for heart attacks, diphenhydramine HCL for allergic reactions to food/insect allergies, calcium carbonate for acid reflux, loperamide for diarrhea, ibuprofen for joint/muscle aches, and the like.)

Many users are told that it is crucially important to carry aspirin at all times, as taking an aspirin at the first sign of a heart attack may significantly increase a chance of living after the heart attack. Having no better option, many users carry two small aspirin pills, wrapped in cellophane, in their wallet. However, many users express the sentiment that this solution is very inconvenient and undesirable, as the pills are generally bulky and do not fit into a wallet easily or comfortably. Further, the cellophane unravels and is not waterproof, so perspiration from sitting on a wallet in hot weather may make them "milky" and unsanitary, and they can fall out of the wallet when the wallet is opened. Furthermore, if one has a medical emergency, it may delay consumption of the asprin if it difficult to locate a suitable beverage to aid in swallowing the pill. There is a further concern that the medicine wrapped in this fashion may be more easily contaminated as the medicine is not sealed. Then there is some concern with tamper-evidence and child-safety.

What is needed is a vehicle to carry a powered medication that addresses the limitations of the prior art.

BRIEF SUMMARY OF THE INVENTION

The present invention provides a vehicle to carry a powered medication that addresses the limitations of the prior art. It includes a system and method. A powder delivery system includes a first panel and a second panel coupled together around a periphery of the panels to form a sealed void therebetween, each the panel having a width and length about equal to a standard credit card width and length, respectively; and a powder, disposed in the void, having a quantity at least about equal to an active dose of the powder; wherein a thickness of the panels with the powder disposed therebetween is not greater than about 0.1 inches and more preferably not greater than about 0.03 inches.

A powder delivery method, includes (a) disposing a powder within a sealed void formed by sealing edges of two powder contamination-resistant panels together, the panels generally about the size of a credit card and the panels with the powder disposed within the sealed void having a thickness not greater than about 0.03 inches, the panels are resistant to tearing, puncturing, and moisture while being flexible and pliable wherein a construction of the panels with the powder disposed therebetween retains a flat profile that further resists premature access to the sealed void and exposure of the powder responsive to compressive forces applied to the panels, the panels including at least two tear-initiation notches for facilitating opening the sealed void to access the powder disposed therein; (b) tearing the panels using one of the tear-initiation notches to expose the void and access the powder; and (c) ingesting the powder from the void.

The present invention offers a powder delivery system and method that is convenient for a man or woman to carry and have available anytime. The user has confidence that the powder will be available in an ingestible condition free from contaminants with reduced chances of environmental degradation.

BRIEF DESCRIPTION OF THE DRAWINGS

FIG. 1 is a plan view of a powder delivery system.

DETAILED DESCRIPTION OF THE INVENTION

The present invention relates to apparatus, systems, and methods that provide a vehicle to carry a powered medication that addresses the limitations of the prior art. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

In a preferred embodiment, an embodiment provides a package as thin as a credit card, that is waterproof, pliable, and easy to fit in one's wallet so they may carry it on their person at all times in case of emergency. The medicine in the packet would be in powder form, so that it would be absorbed much faster than a pill that needs to be swallowed and digested. Providing a durable, pliable, and waterproof sealed container improves the quality of the powder when delivered. With such a container, contamination and moisture is reduced so that spoilage and "clumping" is virtually eliminated. The medication will easily slide out of the packet when opened and the user has more confidence and is better able to depend upon the availability of the medicine should there be an emergency. Furthermore, being a powder more users will be able to ingest the dose without requiring a liquid.

An embodiment of the invention includes a pair of panels generally sized like a standard credit card size (2⅛"×3⅜" or 54×85.6 mm, with a thickness of 30 mils or 0.03"), so that it would easily fit into a credit card slot within a standard wallet. At this size, there is sufficient volume within the card so that normal dosage quantities distributed within the packet in powder form ensures that the card is thin enough to still fit in a wallet card slot without bulk. It is not just thin, but this embodiment of the invention would also be flexible and pliable, so that it would not be bulky or cause discomfort within the wallet, and would not split or break open when sat upon. It may be made from a combination of foil and plastic so that it may be torn open to access the medication, but still durable enough to remain intact within a wallet, and additionally be environmentally protective (e.g., waterproof and sanitary) in order to preserve quality and efficacy of the medication within. The packaging is preferably inert so as to not interact with the medication within. A preferred embodiment provides for a disposable, single dosage solution that is very inexpensive to manufacture while being effective and efficient for the end-user.

It is believed that three times the standard thickness of a credit card (~0.1 inch) makes the product too rigid and subject to bursting or leakage when manipulated. An appeal of the present invention is that it is thin and flexible, capable of being unobtrusively stored in a wallet. A measure of flexibility is that the package be able to be folded in half without a rupturing, tearing, or leakage.

Some embodiments include an optional removable "hangtag" portion which allows it to be easily displayed on a rack or display in a retail setting. This optional hangtag portion is able to be torn off without inadvertently opening the package. With the hangtag removed, the package is about the size of a credit card. Additionally, this embodiment preferably includes two tear notches, so that in the case of an emergency, the user has more than one chance to open the package and get to the medicine within. This card could possibly be printed with logos, advertising information, or public service information which is a unique way to promote a brand by having their logo within one's wallet.

Some medications have small dosage amounts, and it is possible to mix the active ingredient with excipients (or fillers) to add more substance to the medication (so the user does not think it is empty), as well as to improve the taste of the medicine/active ingredients, as well as design the ingredients to be easily soluble in water to make it easy to swallow the medication.

FIG. 1 is a plan view of a powder delivery system 100. System 100 includes a pair of panels 105 sealed around a periphery to form a void 110. A set of pre-defined scores 115 permit an optional hangtag 120 to be separated from the sealed panels 105 prior to installation of the sealed panels 105 within a wallet or other storage.

At least two tear-initiation notches 125 are disposed in the sealed periphery of system 100. A powder 130 is disposed within void 110.

System 100 is generally sized to not be greater than a credit card, including a thickness. It is important that the panels be strong, tear-resistant, and resistant to contamination, while being thin, pliable and flexible all the while being constructed in a way that the panels or the seal will not burst, tear, or otherwise permit powder 130 to prematurely leak out.

Suitable materials for panels 105 include plastic, foil, mylar, laminated/coated paper, combinations of these and other materials that preserve and protect the powder appropriate for the application. These materials are easily resistant to tearing, puncturing, wetting, and contaminating and other environmental degradations. Thus, when it is necessary to dispense powder 130, it can be a challenge to reliably expose void 110 and access powder 130 even in the best of circumstances, and even more challenging in the middle of an emergency situation, particularly when the user believes that a life is in jeopardy.

System 130 includes at least two tear-initiation notches 125 that provide redundancy to a user urgently accessing powder 130 during an emergency. In some cases, a tear direction from tear-initiation notch 125 is unpredictable and may not properly expose void 110 and expose powder 130. System 100 includes at least a second notch 125 to improve reliability when accessing powder 130. While two notches are shown, in some applications it may be that a single notch 125 is sufficient. In other applications, three or more notches may be preferred. A third notch may be added, for example, at an end opposite of the two shown notches.

Hangtag 120 is optional and permits system 100 to be distributed using a well-known vending solution. Units of system 100 may be available in convenient form at a checkout or pharmacy in individual units packaged for resale. The user may detach hangtag 120 from the rest of the powder delivery system 100 using the scores 115 to avoid risk to prematurely exposing powder 130. The size of panels 105 with hangtag 120 detached is generally about the length and width of a credit card. The thickness, with powder 130, is as thin as possible while preserving the strength and durability features.

Powder 130 contributes to the flexibility and pliability and resists promoting bursting in response to compressive loading (e.g., sitting on system 100 when installed into a wallet disposed in a back pocket of user who sits down). Without a couple of large pills, there are not artificial bumps that can cause discomfort when sat upon.

In operation, a user acquires system 100 (which may include optional hangtag 120). When hangtag 120 is present, many users will detach hangtag 120 from system 100 using scores 115. They may desirably detach hangtag 120 to reduce the size for more convenient storage in a wallet or other container.

In the event that the user desires access to powder 130, such as urgent access in case of emergency (e.g., a heart attack and powder 130 is a salicylate acid medicament (e.g., aspirin)), system 100 is removed from the wallet. One of tear-initiation notches 125 is used to access void 110 and expose powder 130. In the event that powder 130 is not exposed, the second notch 125 is used to expose powder 130.

When powder 130 is exposed, user ingests powder 130 from void 110. The user may ingest powder 130 after mixing it with a liquid or other modality to improve its ingestion. However, being a powder, it may be ingested directly from void 110.

Table I below includes some representative examples of dosage/quantities of specific powder types that may be included as part of the present invention. The table is not exhaustive and the quantity identifies a medically significant dose for a collective of substances for use with system 100. The quantities are approximate and are often considered to be a minimum for a medically significant dose, more powder may be used. In some cases, a filler, flavoring, or other additive may be used to enhance an appeal of the product or of the powder or to promote effectiveness or ingestion of the powder. The quantity of powder, together with the panels and construction should not interfere unduly with pliability and flexibility of system 100 to risk a stiffness that could cause the package to rupture prematurely when installed into a wallet. This thickness may vary depending upon various design considerations but should, in general, not be greater than about 0.1 inches and more preferably not greater than about 0.03 inches.

TABLE I 650 milligrams of a salicylate drug
150 mg or more of Aspirin (acetylsalicylic acid) for heart attack (or general pain relief)
250 mg or more of Bismuth subsalicylate for upset stomach reliever and anti-diarrheal (also heartburn, indigestion, nausea)
500 mg or more of Calcium carbonate for use as an antacid
1 mg or more of Loperamide HCl for use as an anti-diarrheal
25 mg or more of Diphenhydramine HCl for an antihistamine and for allergic reaction to foods, insects, or other allergens
50 mg or more of Dimenhydrinate for prevention and treatment of symptoms associated with motion sickness (Nausea, Vomiting, and Dizziness)

TABLE I-continued 200 mg or more of a Ibuprofen for use as a pain reliever, fever reducer, or treatment of migraine headaches
325 mg or more of Acetaminophen for use as a pain reliever or fever reducer
A combination of aspirin, acetaminophen and caffeine for treatment of headache or migraine
Varying dosages of Sugar (sucrose) for diabetics The present invention relates to a powder delivery system, and as noted above, part of the motivation of the present invention is to allow a powder, particularly a medicament, to be safely and conveniently stored and carried in a wallet for access during an emergency. Embodiments of the present invention may include a liquid or gel substance, such as these forms of medicaments.

In the description herein, numerous specific details are provided, such as examples of components and/or methods, to provide a thorough understanding of embodiments of the present invention. One skilled in the relevant art will recognize, however, that an embodiment of the invention may be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures may also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A powder medicine delivery system, comprising:
    a first panel and a second panel coupled together around a periphery of said panels to form a sealed void therebetween, each said panel having a width not greater than about 2 ⅛ inches and length not greater than about 3 ⅜ inches; and
    a powder medicine, disposed in said void, having a quantity at least about equal to an active dose of said powder medicine;
    wherein a thickness of said panels with said powder medicine disposed therebetween is not greater than about 0.1 inches, and wherein said panels are flexible.

2. The powder delivery system of claim 1 wherein said panels are resistant to tearing, puncturing, and moisture.

3. The powder delivery system of claim 2 wherein said panels are made from one or more elements from the group consisting of mylar, foil, plastic, laminated paper, and combinations thereof.

4. The powder delivery system of claim 2 further comprising at least two tear-initiation notches for facilitating opening said sealed void to access said powder medicine disposed therein.

5. The powder delivery system of claim 4 wherein said panels are made from one or more elements from the group consisting of mylar, foil, plastic, laminated paper, and combinations thereof.

6. The powder delivery system of claim 1 wherein said dose is selected from one or more of group consisting of at least about 650 milligrams of a salicylate drug, at least about 150 milligrams of acetylsalicylic acid; at least about 250 milligrams of bismuth subsalicylate, at least about 500 milligrams of calcium carbonate; at least about 1 milligram loperamide HCl, at least about 25 milligrams diphenhydramine HCl, at least about 50 milligrams dimenhydrinate, at least about 200 milligrams non-steroidal anti-inflammatory drug, at least about 325 milligrams acetaminophen, at least about a medically significant dose of acetylsalicylic acid, acetaminophen and caffeine, and at least about a medically significant dose of sucrose, and combinations thereof.

7. The powder delivery system of claim 1 further comprising a detachable hangtag coupled to said coupled panels.

8. The powder delivery system of claim 2 wherein a construction of said panels with said powder medicine disposed therebetween retains a flat profile that further resists premature access to said sealed void and exposure of said powder medicine responsive to compressive forces applied to said panels.

9. A powder delivery method, comprising the steps of:
(a) disposing a powder within a sealed void formed by sealing edges of two powder contamination-resistant panels together, said panels generally having a width not greater than about 2 1/8 inches and a length not greater than about 3 3/8 inches, and said panels with said powder disposed within said sealed void having a thickness not greater than about 0.1 inches, said panels are resistant to tearing, puncturing, and moisture while being flexible and pliable wherein a construction of said panels with said powder disposed therebetween retains a flat profile that further resists premature access to said sealed void and exposure of said powder responsive to compressive forces applied to said panels, said panels including at least two tear-initiation notches for facilitating opening said sealed void to access said powder disposed therein;
(b) tearing said panels using one of said tear-initiation notches to expose said void and access said powder; and
(c) ingesting said powder from said void.

10. The method of claim 9 further comprising:
(d) storing, after said step (a), said panels with said powder disposed therebetween in a wallet placed within a back pocket of pair of pants of a user;
(e) sitting down with said wallet within said back pocket to apply said compressive force;
(f) removing, prior to step (b), said panels with said powder disposed therebetween from said wallet.

11. The method of claim 10 further comprising the steps of:
(g) dispensing, prior to step (d), said panels with said powder disposed therebetween from a distribution system that supports said panels using a detachable hangtag coupled to said panels.

12. The method of claim 9 wherein said powder is a dose of a medicament.

13. The method of claim 12 wherein said dose is selected from one or more of group consisting of at least about 650 milligrams of a salicylate drug, at least about 150 milligrams of acetylsalicylic acid; at least about 250 milligrams of bismuth subsalicylate, at least about 500 milligrams of calcium carbonate; at least about 1 milligram loperamide HCl, at least about 25 milligrams diphenhydramine HCl, at least about 50 milligrams dimenhydrinate, at least about 200 milligrams non-steroidal anti-inflammatory drug, at least about 325 milligrams acetaminophen, at least about a medically significant dose of acetylsalicylic acid, acetaminophen and caffeine, and at least about a medically significant dose of sucrose, and combinations thereof.

14. A medication package, comprising:
a first flexible panel and a second flexible panel coupled together around a periphery of said flexible panels to form a sealed void therebetween, each said flexible panel having a width not greater than about 2 1/8 inches and a length not greater than about 3 3/8 inches; and
a powder medication disposed in said void, having a quantity at least about equal to an active dose of said powder medication;
wherein a thickness of said flexible panels with said powder medication disposed therebetween is not greater than about 0.1 inches.

15. The medication package of claim 14, wherein said first and second flexible panels are made from one or more elements from the group consisting of mylar, foil, plastic, laminated paper, and combinations thereof.

16. The medication package of claim 14, further comprising:
at least two tear-initiation notches for facilitating opening of said sealed void to access said powder medicine disposed therein.

17. The medication package of claim 14 wherein said active dose is selected from one or more of group consisting of at least about 650 milligrams of a salicylate drug, at least about 150 milligrams of acetylsalicylic acid; at least about 250 milligrams of bismuth subsalicylate, at least about 500 milligrams of calcium carbonate; at least about 1 milligram loperamide HCl, at least about 25 milligrams diphenhydramine HCl, at least about 50 milligrams dimenhydrinate, at least about 200 milligrams non-steroidal anti-inflammatory drug, at least about 325 milligrams acetaminophen, at least about a medically significant dose of acetylsalicylic acid, acetaminophen and caffeine, and at least about a medically significant dose of sucrose, and combinations thereof.

18. The medication package of claim 14, further comprising a detachable hangtag coupled to said first and second flexible panels.

* * * * *